(12) United States Patent
Joannes (10) Patent No.: US 7,206,079 B2
(45) Date of Patent: Apr. 17, 2007

(54) APPARATUS AND PROCESS FOR CHARACTERIZING SAMPLES

(75) Inventor: Luc Joannes, Sauveniere (BE)

(73) Assignee: Universite Libre De Bruxelles, Brussels (BE)

( * ) Notice: Subject to any disclaimer, the term of this patent is extended or adjusted under 35 U.S.C. 154(b) by 298 days.

(21) Appl. No.: 10/861,673

(22) Filed: Jun. 4, 2004

(65) Prior Publication Data

US 2005/0036153 A1 Feb. 17, 2005

Related U.S. Application Data

(63) Continuation-in-part of application No. PCT/BE02/00184, filed on Dec. 5, 2002.

(30) Foreign Application Priority Data

Dec. 5, 2001 (EP) ................................ 01870270

(51) Int. Cl.
*G01N 21/45* (2006.01)
(52) U.S. Cl. ..................................... 356/518
(58) Field of Classification Search ............... 356/517, 356/518, 128, 129
See application file for complete search history.

(56) References Cited

U.S. PATENT DOCUMENTS

| | | |
|---|---|---|
| 2,883,900 A | 4/1959 | Svensson |
| 2,977,847 A | 4/1961 | Meyer-Arendt |
| 2,998,719 A | 9/1961 | Rubin |
| 5,515,158 A | 5/1996 | Heineck |

OTHER PUBLICATIONS

International Search Report dated Dec. 6, 2003 for International Application No. PCT/BE02/00184, filed Dec. 5, 2002, now International Publication No. WO 03/048837.

*Primary Examiner*—Gregory J. Toatley, Jr.
*Assistant Examiner*—Marissa J. Detschel
(74) *Attorney, Agent, or Firm*—Knobbe Martens Olson & Bear, LLP (57) ABSTRACT

An apparatus and method for measuring by the Schlieren technique light beam deviations generated by a sample (EV) includes a source (S) of light beam for illuminating the sample (EV) therewith so as to have a transmitted beam. An imaging means is provided (L2, L3) for forming an image of the sample from the transmitted beam. A filtering means acts as a Schlieren filter (SF) for obtaining "Schlieren fringes" from the image. The Schlieren filter (SF) comprises a periodic structure (SFP) of a defined period. A detecting means (CCD) is provided for detecting the Schlieren fringes under operating conditions. The apparatus can also include means to shift the filtering means with a shift $\phi$ by a fraction of the period of the periodic structure thereby shifting the Schlieren fringes, means to acquire a set of at least three successive phase-shifted images; means for reconstructing a mean image of the sample from said collected phase-shifted images using a phase-shifting algorithm used in interferometry, and processing means to calculate by said phase-shifting analysis the optical characteristics, angle and phase of the transmitted beam from said reconstructed image so as to determine the beam deviation angle generated by the sample.

25 Claims, 11 Drawing Sheets

APPARATUS AND PROCESS FOR CHARACTERIZING SAMPLES

CROSS REFERENCE TO RELATED APPLICATIONS

This is a Continuation-in-Part of international patent application No. PCT/BE02/00184, filed on Dec. 5, 2002 claiming priority to European Patent Application No. 01870270.4, filed on Dec. 5, 2001. The entire contents of the above international application is incorporated herein by reference.

BACKGROUND

1. Field of the Invention

The present invention is related to an apparatus and a process for characterising samples. Such samples can be gaseous or liquid volumes or even solids, such as a refractive surface or a transparent volume.

A particular application of said apparatus and process concerns the measurements of the refractive index gradients in samples such as liquids. Other applications such as shape measurements, optical property measurements, non destructive testings can be envisaged.

2. State of the Art

Since the end of the 19th century, the Schlieren technique is commonly used in order to identify and quantify density or temperature gradients which may occur in a sample or experimental volume.

To summarize, the Schlieren technique consists in measuring relight beam deviations such density or temperature gradients induce. A conventional Schlieren arrangement comprises a light source associated with a slit, a filter known as the "Schlieren filter" and located in front of a camera, for taking an image of a sample, said sample being placed between the light source and the Schlieren filter. Any refractive index gradient in the studied sample will deviate the light beam by a deviation angle $\alpha$ and the spot on the Schlieren filter, which is preferably a knife-edge, will be displaced, thereby resulting in a modification of the light intensity reaching the camera.

The success of said technique, which consists in measuring light beam deviations such gradients induce, lies on its high sensitivity, its low cost and its easiness of implementation.

The main drawback of this technique lies in the necessity to calibrate the complete measurement apparatus to extract quantitative data from it.

Furthermore, the resolution of measurement is generally low.

Aims of the Invention

The present invention aims to provide an apparatus and a method that do not present the technical drawbacks of the state of the art.

More precisely, the present invention aims to provide an apparatus and a method for characterising properties of samples. Such samples can be gaseous or liquid volumes or even solids.

The present invention also aims to provide an apparatus and a method which are adapted to provide high resolution measurements.

Another aim of the present invention is to provide an apparatus and a method which are easy to use and of low cost.

SUMMARY OF THE INVENTION

Embodiments of the present invention relate to an apparatus for measuring by the Schlieren technique light beam deviations generated by a sample, said apparatus comprising:
- a source of light beam for lighting up said sample therewith so as to have a transmitted beam;
- imaging means for forming the image of said sample from said transmitted beam;
- filtering means acting as a Schlieren filter for obtaining from said image, in operating conditions, an optical signal called "Schlieren fringes"; whereby the Schlieren filter comprises a periodic structure of a defined period;
- detecting means for detecting said Schlieren fringes in operating conditions;

wherein the apparatus further comprises:
- means to shift the filtering means with a shift $\phi$ by a fraction of the period of the periodic structure thereby shifting the Schlieren fringes,
- means to acquire a set of at least 3 successive phase-shifted images;
- means for reconstructing a mean image of the sample from said collected phase-shifted images using a phase-shifting algorithm used in interferometry,
- processing means to calculate by said phase-shifting analysis the optical characteristics, angle and phase of the transmitted beam from said reconstructed image so as to determine the beam deviation angle generated by the sample.

Preferably, the Schlieren filter corresponds to a grating filter.

Preferably, the Schlieren filter corresponds to a linear grating filter.

Preferably, the said linear grating filter is a Ronchi grating.

Preferably, the Schlieren filter corresponds to a sinusoidal grating filter.

Preferably, the Schlieren filter corresponds to a grating filter having circular rings or non regular shape.

According to a preferred embodiment, the phase-shifting means comprise moving means for moving the Schlieren filter relatively to the transmitted beam produced by the sample so as to create in operating conditions a phase-shift in the transmitted beam.

According to another preferred embodiment, the filtering means comprises a liquid crystal display on which, in operating conditions, the periodic structure can be generated, said liquid crystal display being coupled to an aperture of a defined diameter, said diameter being dependent from the period of the periodic structure.

Preferably, the phase-shifting means correspond to the liquid crystal display on which in operating conditions phase-shifted periodic elements are successively generated.

Preferably, the detecting means correspond to a camera.

Another embodiment of the present invention is related to a method for detecting and measuring light beam deviations created by a sample using the apparatus as described here above.

In said case, the method comprises the steps of:
- providing a sample to be studied;
- obtaining, by combining the Schlieren technique and the phase-shifting technique, a set of successive phase-shifted images of the sample;
- collecting said phase-shifted images;

reconstructing a mean image of the sample from said collected phase-shifted images using phase-shifting analysis;

calculating by phase-shifting analysis the optical characteristics, angle and phase of the transmitted beam from said reconstructed image so as to determine the deviation angle generated by the sample.

Another embodiment of the present invention is an apparatus for measuring by the Schlieren technique light beam deviations generated by a sample, said apparatus comprising:

a light source which provides a transmitted beam;

components which form an image of said sample from said transmitted beam;

a Schlieren filter comprising a periodic structure of a defined period;

a detector which detects Schlieren fringes generated by said Schlieren filter;

components which shift the Schlieren fringes, components which acquire a set of at least three successive phase-shifted images;

component which reconstruct a mean image of the sample from said phase-shifted images using a phase-shifting algorithm used in interferometry; and a processor which calculates by said phase-shifting analysis the optical characteristics, angle and phase of the transmitted beam from said reconstructed image so as to determine the beam deviation angle generated by the sample.

BRIEF DESCRIPTION OF THE DRAWINGS

FIGS. 15 to 19 correspond to the results obtained with an apparatus of the invention used in reflection mode in order to measure the surface shape of a tested liquid in a Marangoni-Bénard test. In particular

FIGS. 20 to 24 correspond to the results obtained from a Marangoni-Bénard test similar to the one performed in FIGS. 15 to 19, but at a different position in the experimental cell where the liquid-gas interface deformation is higher. In particular.

FIGS. 25 to 29 correspond to the results obtained for a tested lens with an embodiment of the apparatus according to the present invention comprising a liquid crystal display (LCD) generating a circular filter.

FIG. 35a corresponds to images as acquired with said particular apparatus and FIG. 35b corresponds to said images after processing.

DETAILED DESCRIPTION OF THE STATE OF THE ART

Figure 1:
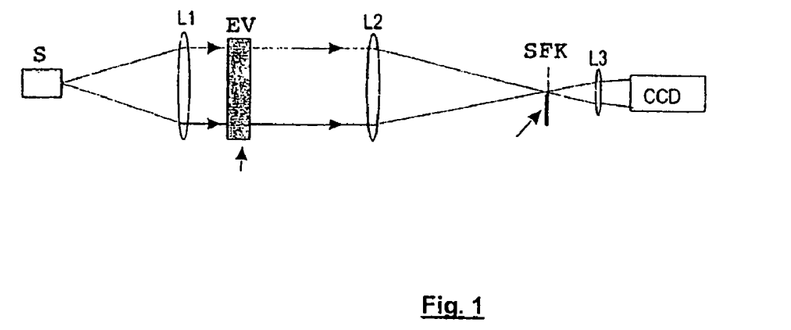
FIG. 1 represents the different optical elements in a conventional apparatus for performing the Schlieren technique according to the state of the art.

A conventional Schlieren arrangement is represented in FIG. 1. Said arrangement according to the state of the art corresponds to a transmission setup using an extended light source associated with a diaphragm. The diverging beam emitted by the source S is collimated by the lens L1. The beam is then passing through the sample being an experimental volume EV, and is focused by the so-called Schlieren lens L2. The Schlieren filter SF is located at the focal plane of L2. L3 is then used to image the center of the experimental volume on the sensor of the camera CCD. Any refractive index gradient inside the sample EV will deviate the beam by an angle $\alpha$ and the spot on the Schlieren filter (image of the source) will be displaced. It will result in a modification of the light intensity reaching the camera.

Figure 2:
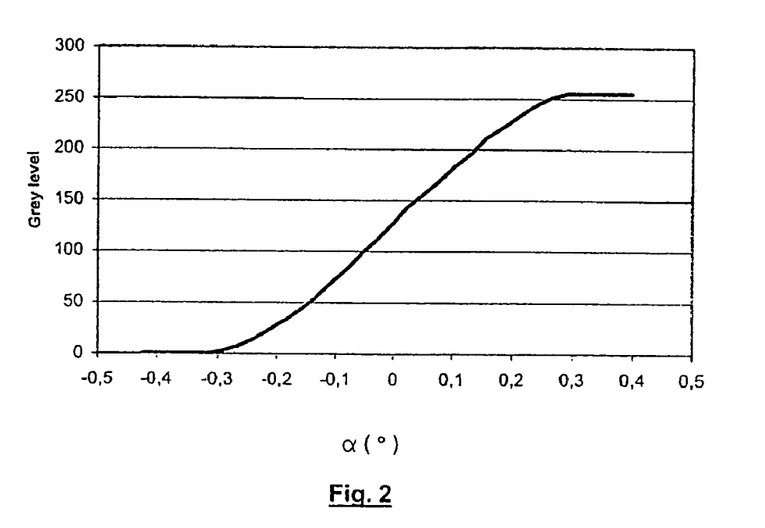
FIG. 2 represents a typical response curve of a sample placed in a conventional Schlieren apparatus according to the state of the art (as illustrated in FIG. 1) (Gray level (Gl) as a function of the beam deviation angle ($\alpha$)).

In said conventional Schlieren arrangement, the Schlieren filter is a knife-edge filter SFK. The range of beam angle that can be measured is defined by the size of the image of the diaphragm in the plane of the Schlieren filter. The angle deviation a according to the Gray level Gl is coded by a quite linear curve in the working range as illustrated in FIG. 2. Out of this range, no intensity variation is obtained.

This experimental fact can be mathematically explained as follows. The intensity measured on the camera plane can be expressed as a function of the deviation angle:

$$I(x,y)=f(\alpha(x,y),a,b,\ldots) \quad \text{(Eq. 1)}$$

In the case of a pure linear relation between the deviation angle and the intensity measured on the camera, Eq. 1 becomes:

$$I(x,y)=a\cdot\alpha(x,y)+b° \quad \text{(Eq. 2)}$$

This expression is valid for $\alpha_{min} \leq \alpha \leq \alpha_{max}$. Out of this range the intensity is constant. It can be noted that, theoretically, a pure linear relation is obtained with a light source equipped with an infinite slit instead of the diaphragm.

DETAILED DESCRIPTION OF SEVERAL EMBODIMENTS OF THE INVENTION

Figure 3:
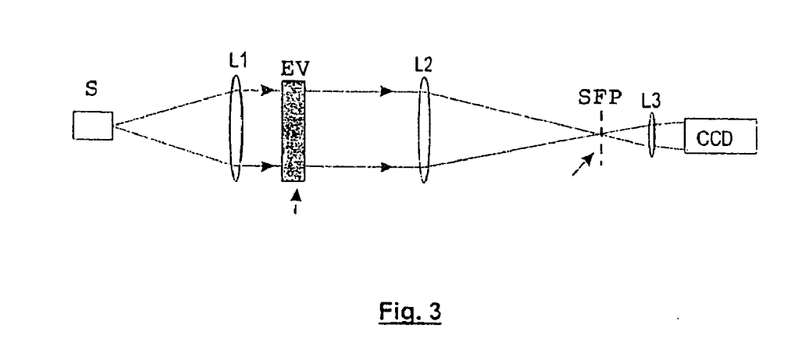
FIG. 3 represents the different optical elements as arranged in an apparatus according to one preferred embodiment of the present invention.

First Embodiment:

FIG. 3 gives a first preferred embodiment of the different optical elements as arranged in the apparatus according to the present invention.

In said embodiment, the Schlieren filter is not a knife-edge filter as described in the state of the art, but is a binary Ronchi grating (SFP) having a succession of transparent and absorbing lines. Such a filter allows the repetition of the basic knife-edge filter effect many times in the filter plane.

Figure 4:
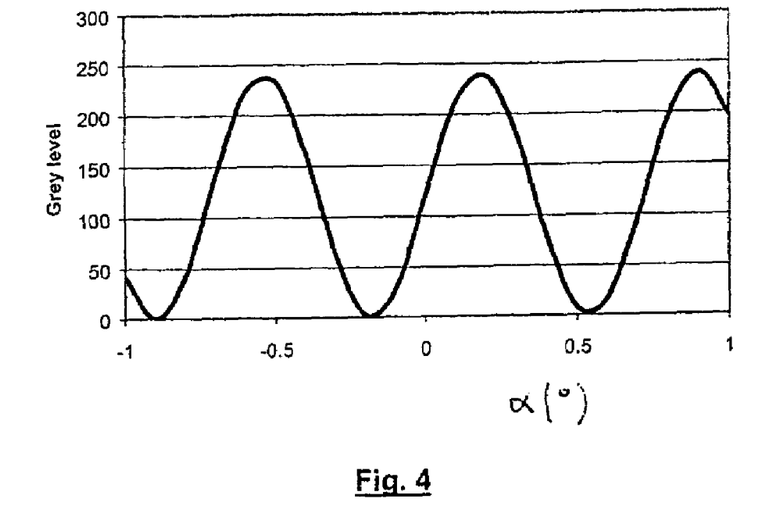
FIG. 4 represents a typical response curve of a sample when placed in an apparatus according to the present invention (as illustrated in FIG. 3).

By an adequate choice of the grating period, it is possible to arrange the Schlieren system in such a way that the angle deviation ($\alpha$) according to the Gray level (Gl) is coded over a wide angle range by a sinusoidal function as defined in Equation 3 and illustrated in FIG. 4.

In other words, the apparatus of the invention is conceived so as to generate by that way Schlieren fringes (by reference with the fringes obtained with interferometric techniques), the intensity of one fringe being expressed as a function of the phase shift $\phi$ and of the deviation angle a generated by the variation of the refraction index inside the studied sample volume:

$$I(x,y)=I_0(x,y)\{1+\gamma(x,y)\cos(p\alpha(x,y)+\phi)\} \quad \text{(Eq. 3)}$$

As shown by Eq. 3, the period of these fringes called hereunder Schlieren fringes is directly linked to the period of the Ronchi grating filter called hereunder grating periods.

It should be noted that the apparatus according to the invention is not restricted to the ones comprising line gratings. Said apparatus may also comprise other types of gratings, such as a calculated periodic structure or design (circular grating, etc.).

However, an important common feature of the present apparatus is that the period of the Schlieren filter is at least of about 0.5 mm. Indeed, below 0.5 mm, diffraction effects introduce noise into the Schlieren fringe images. There is no upper limit value for the period of the Schlieren filter, except that for long periods and relatively small beam deflections, less than one fringe can be seen thereby limiting the reachable precision.

In practice, the period of the Schlieren filter will be adapted to the highest light beam deflection expected with the type of samples tested.

Another important common feature of the present apparatus is that the dimension of the source should be chosen in accordance with the period of the Schlieren filter so as to obtain reliable sinusoidal fringes on the camera, and thus reliable and accurate measurements.

If R is defined as the ratio of the distance d (the source dimension) and the filter period $\Lambda$ (R=d/$\Lambda$), preferred ratios in the present apparatus are the following, depending on the error rate to be reached and thus the level of data accuracy:

0.55<R<1.12 for an error rate lower than 25%;
0.60<R<0.87 for an error rate lower than 20%;
0.64<R<0.82 for an error rate lower than 15%;
0.68<R<0.79 for an error rate lower than 10%.

Figure 33:
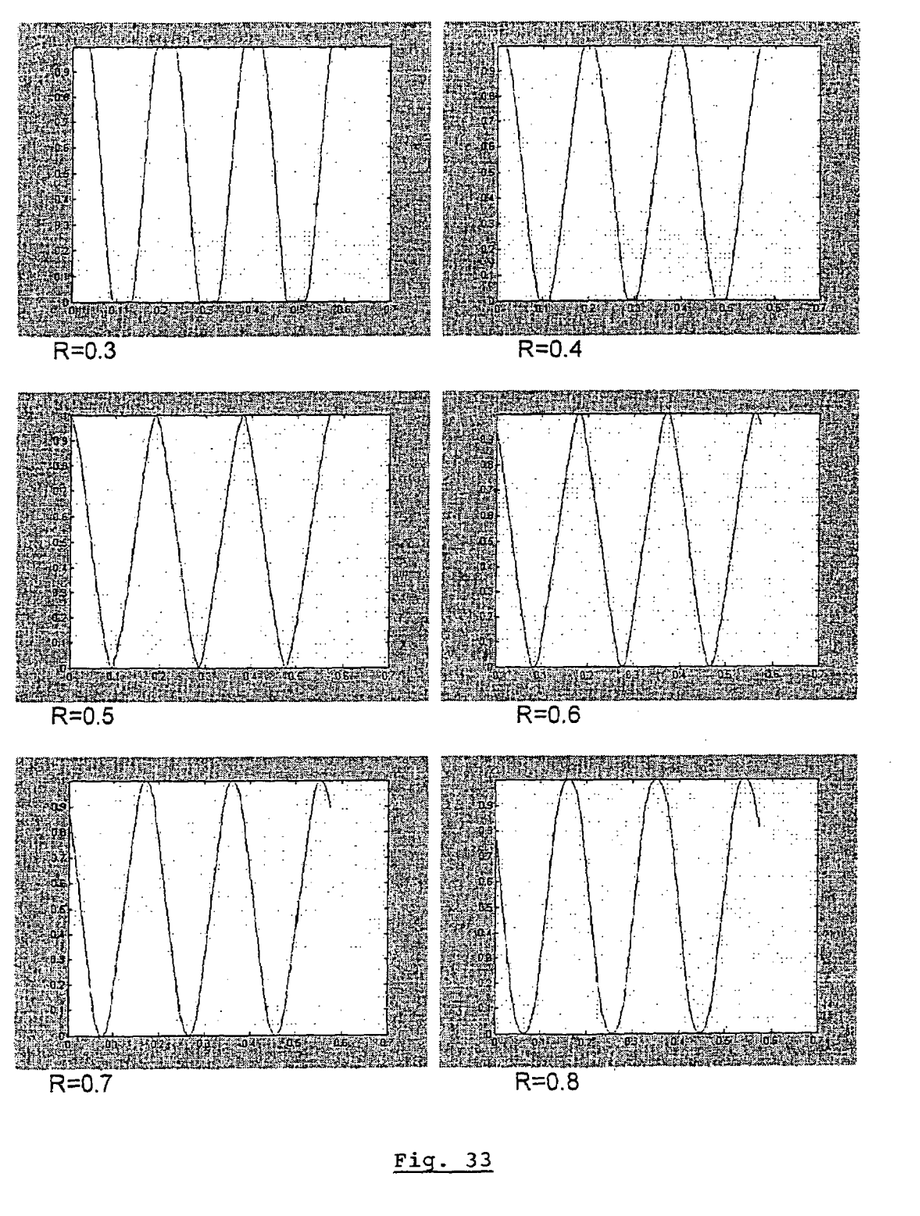
FIG. 33 represents the response of an apparatus according to one embodiment of the invention for different ratios R (source dimension/Schlieren filter period).

FIG. 33 presents the response of the apparatus for different values of the R ratio.

It has been shown that for values of R of about 0.7, the response of the apparatus is very close to a sinus.

Once the Schlieren fringes are generated by the sample, they can be shifted by shifting the periodic Schlieren filter (displacement of the grating in its plane by a fraction of its period, or phase-shifting of the periodic structure displayed on the LCD, see below). A set of phase-shifted images (generally between 3 and 5) is acquired and the phase is calculated using a phase-shifting algorithm as generally used in interferometry [see P. Hariharan et al., Digital phase-shifting interferometry: a simple error-compensation phase calculation algorithm, App. Opt., 26(13), 2504–2506 (1987)]. The modulo 360° phase is then unwrapped and converted in beam deviation angle.

Concretely, for example, the implementation of the process for determining the variations of the refraction index in a sample volume using the apparatus according to the present invention comprises the step of acquiring a set of images (at least 3) with a shift $\phi$ of the grating by a fraction of the grating period. Than, the phase is calculated with a conventional algorithm used in phase-shifting interferometry and unwrapped according to well-known techniques used also in interferometry. After this step, the angular deviation $\alpha$ is automatically quantified: the phase is directly converted into angular deviation since the period of the grating is known (linear relation). Advantageously, no additional calibration is required and a high resolution is obtained since the beam deviation is deduced from phase calculation.

Figure 5:
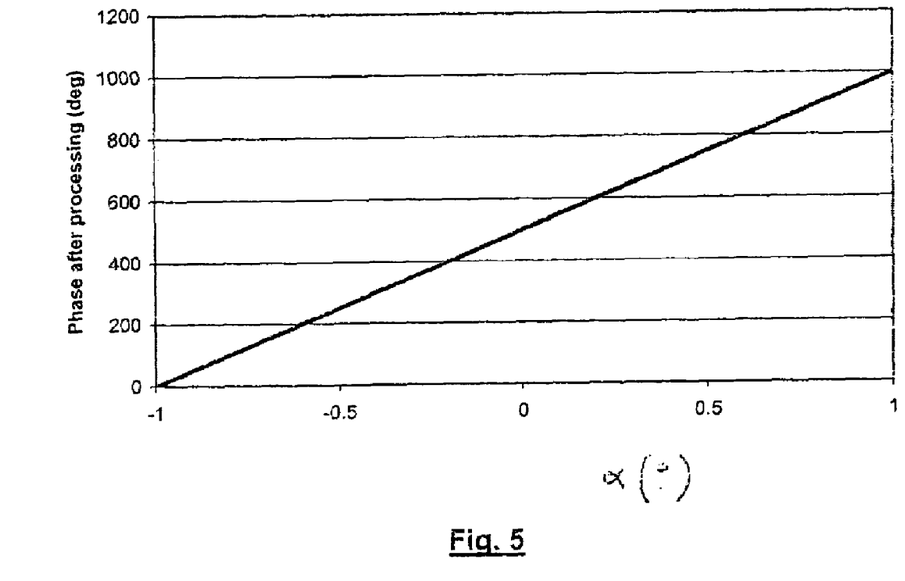
FIG. 5 represents the phase ($\phi$) as calculated from the response curve of FIG. 4 as a function of the deviation angle ($\alpha$).

FIG. 5 presents a typical phase analysis calculated from Schlieren fringes of FIG. 4 which were initially obtained with an apparatus according to the invention. We can observe the linear behaviour of the beam deviation ($\alpha$) according to the phase after processing.

Once the phase analysis has been made, the next step of the process comprises conventional processing of Schlieren data (mainly integration) in order to calculate the refractive index in the fluid or the surface shape.

Figure 6:
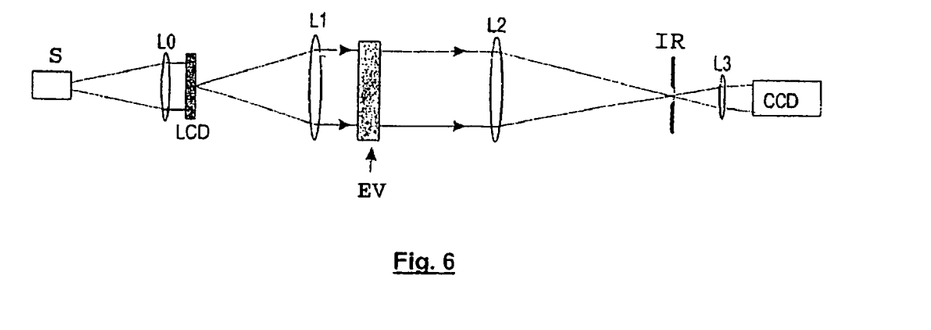
FIG. 6 represents the different optical elements as arranged in an apparatus according to a second embodiment of the present invention.

Second Embodiment:

In another embodiment, the Schlieren filter in the apparatus according to the invention is not a Ronchi grating but comprises a Liquid Crystal Display (LCD) as illustrated in FIG. 6, preferably coupled to an aperture such as an iris (IR), of defined diameter. In operating conditions, a periodic element such as a grating, is generated on the LCD.

Said embodiment offers the particular advantage of allowing a more flexible analysis of the data, since the shift can be controlled faster with a personal computer and the Schlieren measurement can be done in different directions, to measure for example two components of beam deviation, in a fraction of one second.

Moreover, with a LCD, other grating shape like circular rings can be implemented by calculation, even with a phase-shift.

It should be noted that in the embodiment illustrated in FIG. 6, the positions of the LCD and the iris have been inverted in order to reduce the effect of diffraction produced by the LCD, but the two positions are conjugated and there are no difference in the physical working principle of the apparatus.

It should also be noted that in said embodiment the process and the final results obtained thereby are quite insensitive to any intensity variation in the illumination of the LCD (as far as the intensity distribution is constant with time).

Further Embodiments

EXAMPLE 1

Experimental Set-Up to Verify the Phase Shift Schlieren Principle

Figure 7:
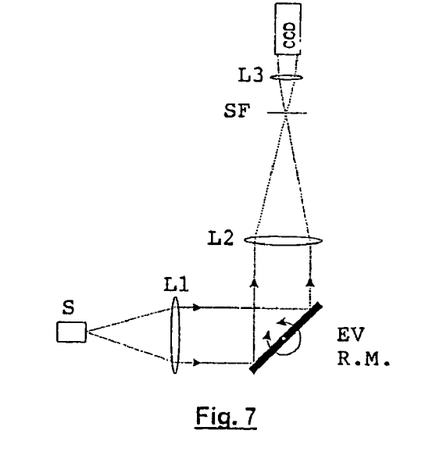
FIG. 7 represents the experimental set-up according to another preferred embodiment of the present invention.

In the present embodiment, the sample is a rotating mirror (RM). Therefore, a device as represented in FIG. 7 and including a circular iris instead of the slit and a Ronchi grating instead of the sinusoidal one has been used. It has been verified that with the iris diameter of half of the period of the grating, one can get a sinusoidal intensity variation with the beam angle. The usual sample volume has been replaced by a rotating mirror (RM) and the measurement of the Schlieren fringe period has been done.

Figure 8:
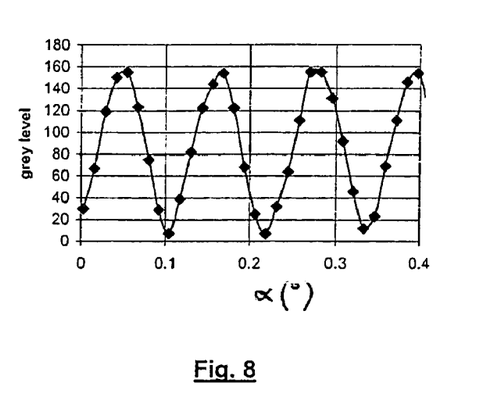
FIG. 8 represents the measured intensity variation as measured using the set-up of FIG. 7 with a rotation angle and a grating of 1.2 mm period.
Figure 9:
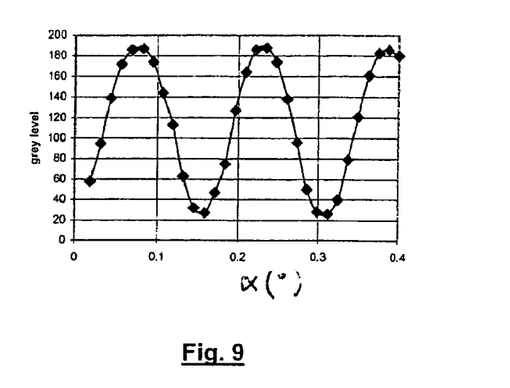
FIG. 9 represents the measured intensity variation as measured using the set-up of FIG. 7 with a rotation angle and a grating of 1.6 mm period.

The iris diameter has been fixed to the minimum (~0.8 mm). The focal length of L1 and L2 are 300 mm. Two grating periods have been tested (1.2 mm and 1.6 mm). Corresponding intensity variations are given in FIG. 8 and FIG. 9.

After fitting with a sinusoidal function, it has been found that the periods are 0.115° for the grating of 1.2 mm period and 0.154° for the 1.6 mm period grating.

With a given grating, it has been observed that the Schlieren fringe period is not changing when the iris diameter is changed. Only the fringe modulation and the fringe shape are altered.

EXAMPLE 2

Measurement of the Curvature Radius of a Lens Surface

Figure 10:
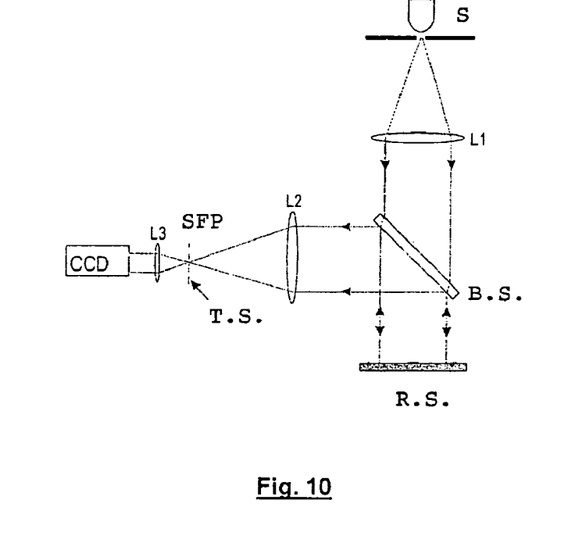
FIG. 10 represents an apparatus according to a further embodiment of the present invention as used for measuring the shape and the curvature radius of a lens surface.

A device as in Example 1 is used in reflection phase shift Schlieren mode (see more precisely FIG. 10). In that case the sample is a reflective surface (RS), such as a surface of a lens having a long focal (1 m). The beam is therefore split through a beam splitter (BS) into two beams. The beam passing through the beam splitter is directed to the reflecting surface where it is redirected to the beam splitter and reflected partially to the imaging and filtering optics. The Ronchi grating is placed on a translation stage (TS) to implement the phase shift.

Figure 11:
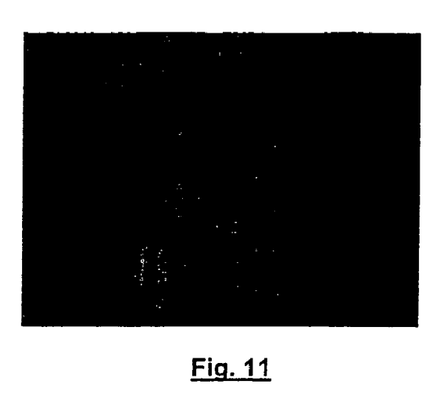
FIG. 11 represents Schlieren fringes obtained with the embodiment of FIG. 10.
Figure 12:
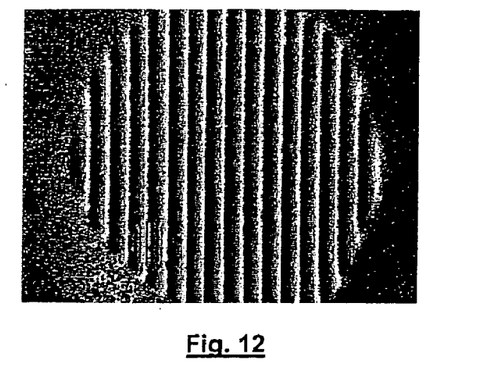
FIG. 12 represents the corresponding calculated phase.

Schlieren fringes obtained by using the above set-up (lens+linear Ronchi grating as filter) are given in FIG. 11. The typical width of the picture corresponds to a field of view of 40 mm. After having acquired 5 fringe images shifted by 90°, the phase has been calculated (FIG. 12), then a simple processing has been done on one line: the unwrapped phase has been converted in angular value.

Figure 13:
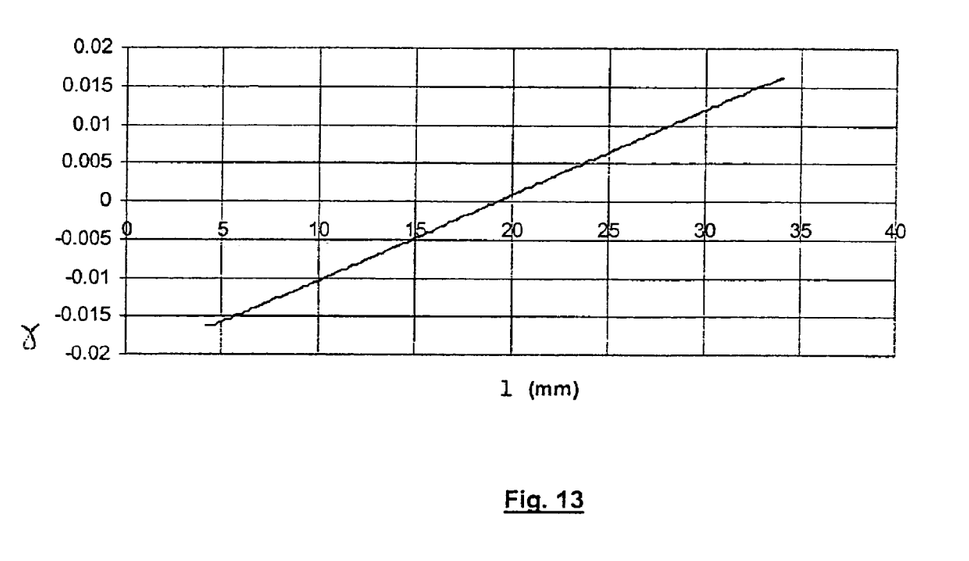
FIG. 13 represents the obtained deviation angle ($\alpha$) as a function of the position on the lens (l).

After the spatial calibration, and after considering the center of the picture as the center of the lens, the deviation angle ($\alpha$) has been plotted versus the position (l) (FIG. 13).

Figure 14:
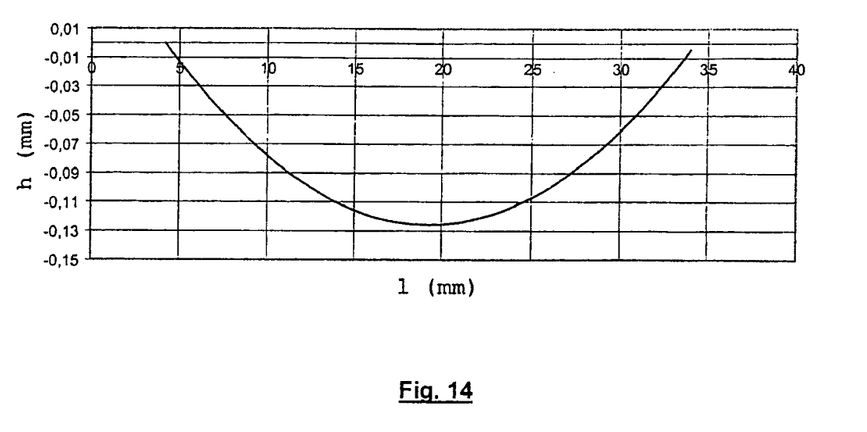
FIG. 14 represents the profile of the lens resulting from the data analysis of FIGS. 11–13.

Then, the profile of the lens has been calculated by integration of the deviation angle (FIG. 14). Moreover, from the slop of the curve in FIG. 13, the curvature radius of the lens representing the height (h) versus the position (l) can be deduced. In the present example, the curvature radius of the lens was deduced to be 900 mm by the above methodology, while the measured curvature radius with a spherometer was 925 mm. The difference is only 2.8%.

This device has also been used to measure the beam deviation produced by the lens (set-up in transmission). The focal length has been deduced. Aberrations could also be evaluated.

EXAMPLE 3

Application in Fluid Physics

The set-up in reflection has been used to measure the liquid surface shape in a Marangoni-Bénard test. Surprisingly, very interesting results have been obtained. In the center of the BAMBI cell, hexagons have been generated by heating from below.

Figure 15:
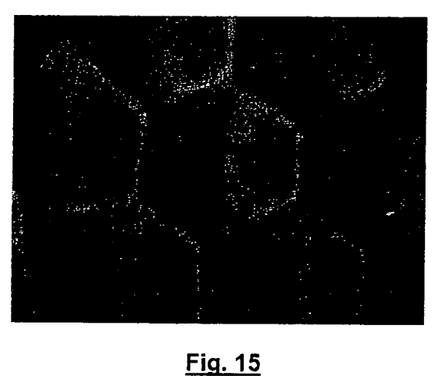
FIGS. 15 and 16 represent two of the five captured images while FIGS. 17 and 18 correspond to the calculated and the unwrapped phase, respectively.
Figure 16:
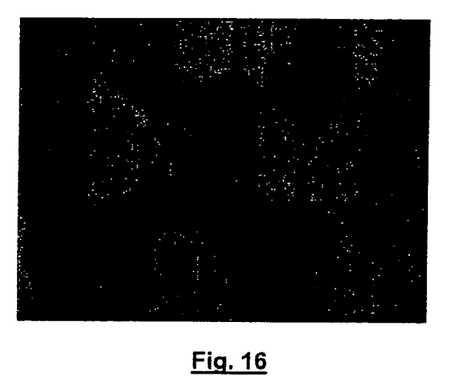
Figure 17:
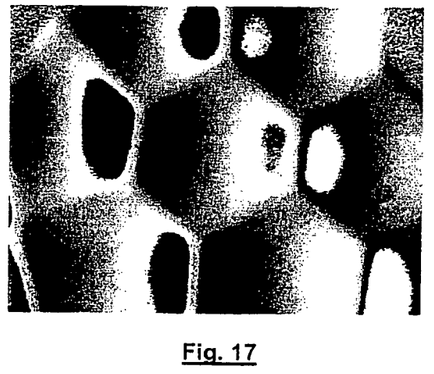
Figure 18:
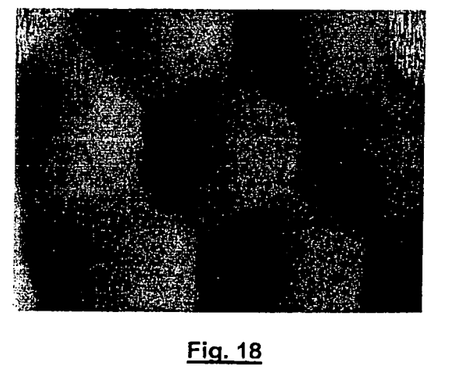

The results are presented on FIG. 15 and FIG. 16, which are two of the five shifted images captured. FIG. 17 represents the calculated phase, and FIG. 18 represents the unwrapped phase.

Figure 19:
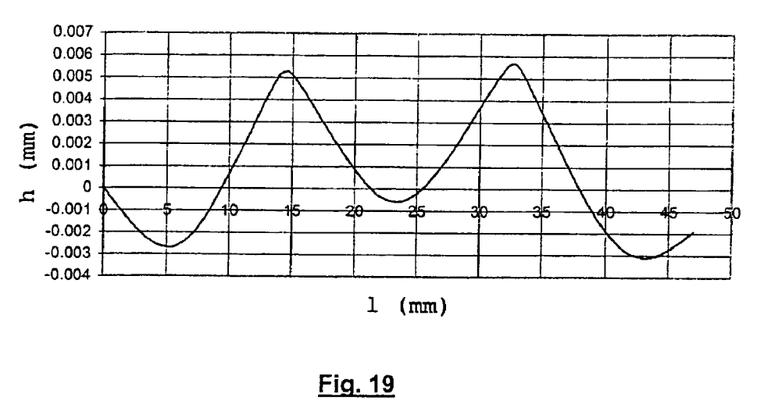
FIG. 19 represents the corresponding profile of the liquid-gas interface on one line.

One horizontal line has been processed like for the lens. FIG. 19 presents the profile of the liquid-gas interface (height (h) versus the position (l)).

Figure 20:
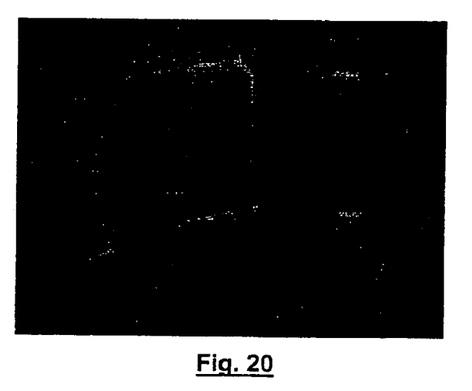
FIGS. 20 and 21 represent two of the five captured images while FIGS. 22 and 23 correspond to the calculated and the unwrapped phase precisely.
Figure 21:
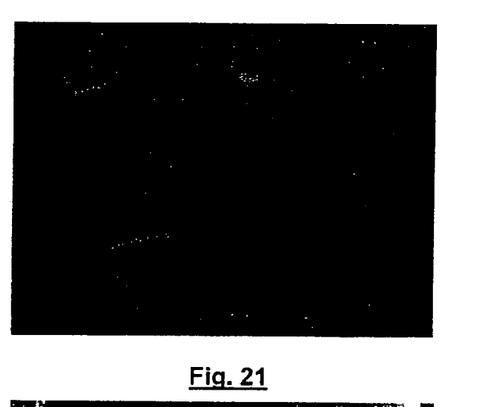
Figure 22:
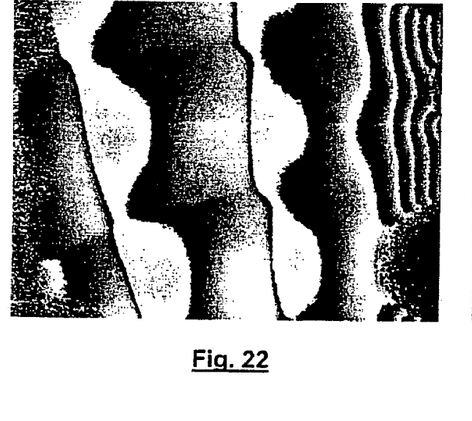
Figure 23:
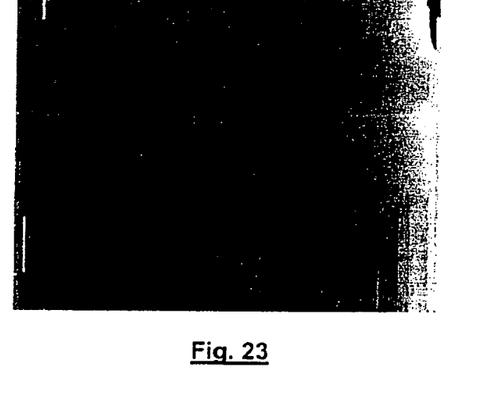
Figure 24:
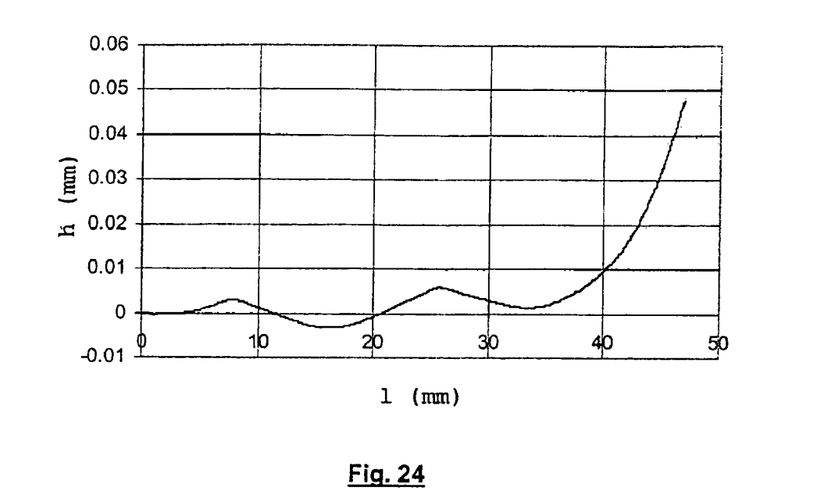
FIG. 24 represents the corresponding profile of the liquid-gas interface on one line.

FIGS. 20 to 24 correspond to the results obtained from a Marangoni-Bénard test similar to the one performed in FIGS. 15 to 19, but at a different position in the experimental cell where the liquid-gas interface deformation is higher. In particular, FIGS. 20 and 21 represent two of the five captured images while FIGS. 22 and 23 correspond to the calculated and the unwrapped phase, respectively. FIG. 24 represents the profile of the liquid-gas interface on one line giving the height (h) versus the position (l). As seen, close to the border of the cell, convection cells of different shapes are observed but also an important surface deformation (certainly due to an under fill of the cell). Deformations up to 50 μm have been measured.

EXAMPLE 4

Implementation of the LCD

The Phase-shift Schlieren device including the LCD (FIG. 6) has been implemented and tested. To show the powerful and the flexibility of the technique, some circular Ronchi shapes have been generated with the LCD, and a lens of long focal length has been introduced instead of the experimental volume.

Figure 25:
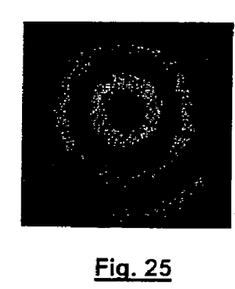
FIGS. 25 and 26 represent two of the five captured images.
Figure 26:
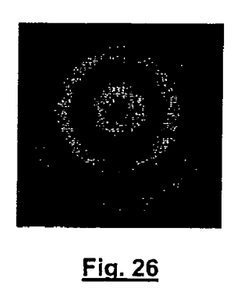
Figure 27:
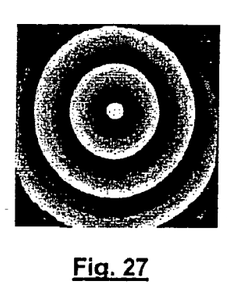
FIGS. 27 and 28 correspond to the calculated and unwrapped phase, respectively.
Figure 28:
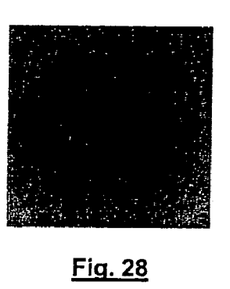
Figure 29:
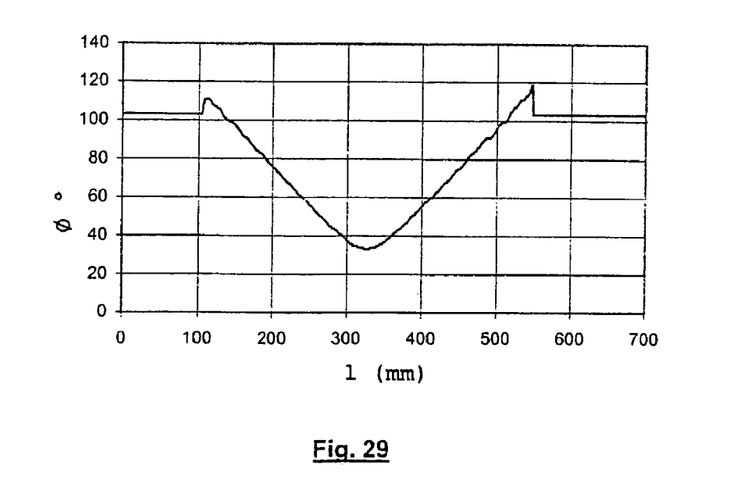
FIG. 29 represents the corresponding profile of the unwrapped phase.

Two Schlieren fringe images as obtained are given in FIG. 25 and FIG. 26. Wrapped and unwrapped phase are in FIG. 27 and FIG. 28. A profile of the unwrapped phase is plotted in FIG. 29 representing the unwrapped phase versus the position (in pixel).

Figure 30:
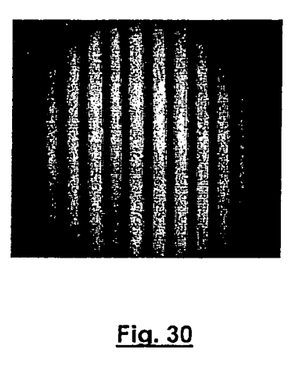
FIG. 30 gives Schlieren fringes as obtained with an apparatus according to one embodiment of the invention, said apparatus including a LCD with a single cylindrical lens.

From such measurements, the focal length of the lens can be deduced, but it is also possible to localize the center of the lens (possible applications in system alignments) and detect aberrations of the lens, in particular circularity error can be rapidly detected. For illustration purposes of the last point, it can be seen in FIG. 30, the Schlieren fringe generated by a cylindrical lens, still with a circular Ronchi grating generated by the LCD. For a perfect cylindrical lens, the Schlieren fringes are perfect lines.

Figure 31:
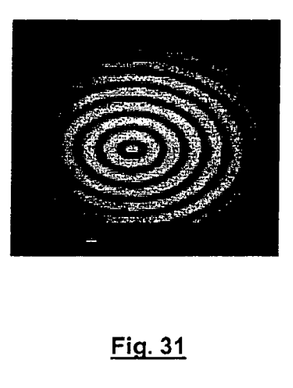
FIG. 31 represents Schlieren fringes as obtained with two cylindrical lenses of different focal length with their axes at 90°.
Figure 32:
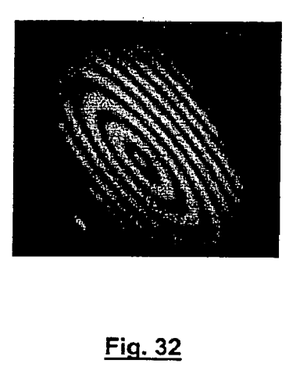
FIG. 32 represents the Schlieren fringes as obtained with the same cylindrical lenses as in FIG. 31 but axes close to 45°.

FIG. 31 gives Schlieren fringes obtained with two cylindrical lens of different focal length with axis at 90°, and FIG. 32 is obtained with the same cylindrical lenses but axis close to 45°.

Therefore, comparatively to the prior art, the dynamic range is not fundamentally different than the one of conventional Schlieren apparatus, and it is limited by the vigneting introduced by the limited diameter of lenses mainly.

EXAMPLE 5

Apparatus Adapted to the Study of Fast Phenomena

The present invention also concerns an apparatus and a method especially adapted to real-time measurements in order to study fast phenomena in a sample (fast comparatively to the acquisition rate of the camera).

Figure 34:
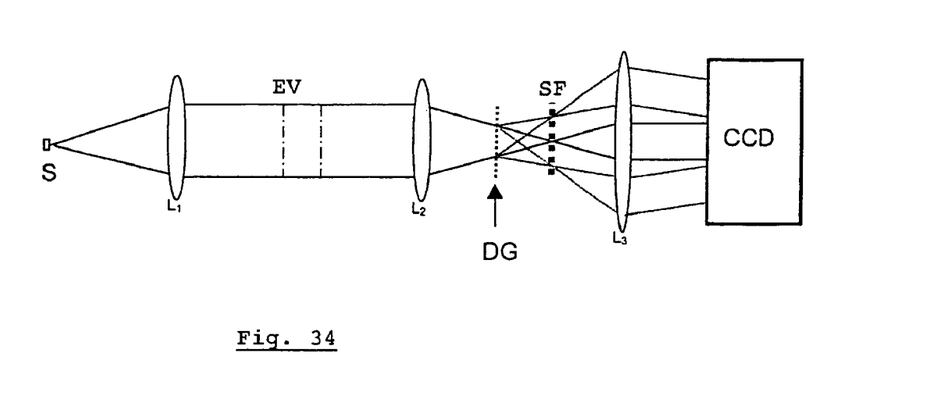
FIG. 34 represents a particular embodiment of an apparatus according to the present invention adapted to the study of fast phenomena.

Comparatively to the apparatus as disclosed above, the apparatus in this particular embodiment further comprises a diffraction element, such as a diffraction grating DG in the optical path as illustrated in FIG. 34.

This diffraction grating DG is located between the lens L2 and the Schlieren filter SF in such a way as to split the beam coming from the lens L2 into three beams corresponding to one not deviated beam and two diffracted beams, one on each side.

The different elements of said apparatus are arranged relatively to each other so that said three beams are spatially shifted when encountering the Schlieren filter SF, and produce the phase-shifting of the images, which was previously obtained by displacement of the Schlieren filter F. In other words, due to the different angle between the three beams, three images of the studied sample are directly created on the camera.

Figures 35A, 35B:
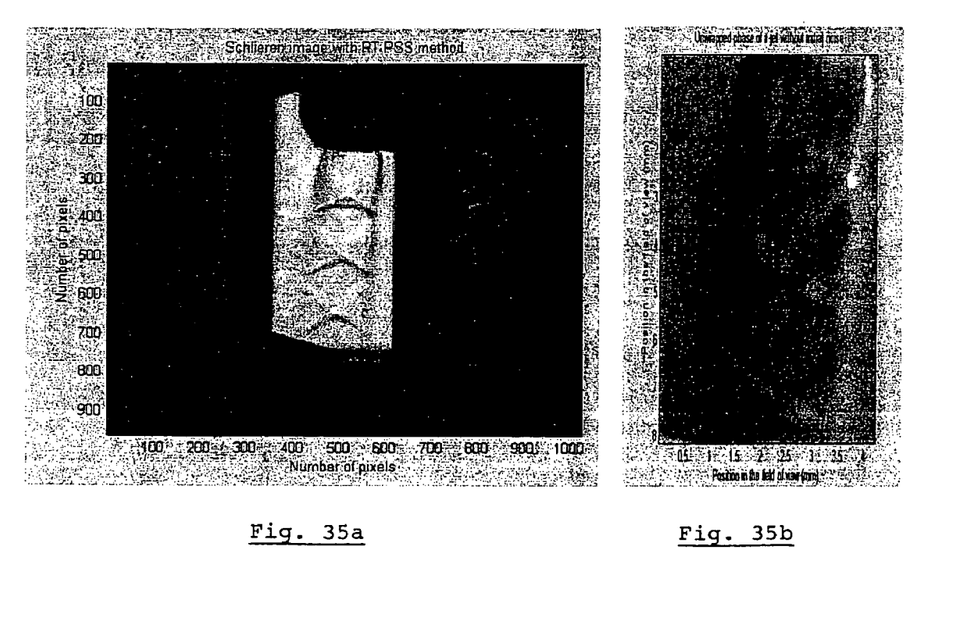

An example of images acquired with this embodiment of the apparatus is given in FIG. 35a The corresponding processed images are given in FIG. 35b.

The conditions to be respected concerning the dimension of the source and the period of the Schlieren filter are the same as disclosed above for the other embodiments.

In addition, the period of the diffraction element, that is of the diffraction grating in this embodiment, is preferably be chosen in such a way that the diffracted orders are spatially separated on the image sebsir (camera). Depending on the apparatus configuration, the period of the diffraction element is preferably comprised between about 10 lp/mm and 150 lp/mm.

Furthermore, the distance between the diffraction grating and the Schlieren is preferably chosen so as to ensure an adequate (Schlieren) phase-shift between the diffracted orders. Depending on the apparatus configuration, said distance is preferably comprised between about 1 mm and about 100 mm.

Advantages of the Present Apparatus and Method

As a conclusion, the apparatus and process according to the invention present several advantages over the prior art.

One of said advantages is that the present technique allows a high-resolution measurement due to the fact that the beam deviation is deduced from a phase measurement instead of direct deviation measurement from intensity variation. Typical phase measurement resolution is at least 20 times better than the fringe period, e.g. for an equivalent period of 0.1°, the angular resolution is better than 0.005°, whatever the dynamic range of the set-up.

Comparatively, in conventional systems, the resolution is limited by the number of digitalization of the imaging systems (e.g. angular range/256 for a conventional CCD and frame grabber system).

Another advantage of the technique of the present invention is its flexibility:
 auto-calibration by the selection of the period of the Schlieren filter;
 no 'Schlieren saturation' introduced by the filter;
 full control by a PC;
 possibility to adapt the Schlieren filter to the type of measurement, and deviation profiles.

Moreover, when the apparatus comprises a LCD, one gets additional possibilities:
 insensitivity of the measurement to source intensity non uniformity;
 possibility to repeat measurements with different sensitivity vectors.

In addition, the interest in an apparatus able to work in real-time as disclosed above is obvious.

The experimental results already obtained demonstrate that the Phase-shifting Schlieren tends to reduce the gap of measurement, in terms of resolution and accuracy, always empty between interferometry and conventional Schlieren; the latter having been insufficiently sensitive with low resolution, the former being very sensitive but with a limited range of measurement.

What is claimed is:

1. An apparatus for measuring by the Schlieren technique light beam deviations generated by a sample, said apparatus comprising:
 a source of light beam for lighting up said sample therewith so as to have a transmitted beam;
 imaging means for forming an image of said sample from said transmitted beam;
 a Schlieren filter for obtaining from said image, in operating conditions, an optical signal called Schlieren fringes; wherein the Schlieren filter comprises a periodic structure of a defined period;
 detecting means for detecting said Schlieren fringes in operating conditions;
 wherein the apparatus further comprises:
 means to shift the Schlieren filter with a shift $\phi$ by a fraction of the period of the periodic structure thereby shifting the Schlieren fringes,
 means to acquire a set of at least three successive phase-shifted images;
 means for reconstructing a mean image of the sample from said collected phase-shifted images using a phase-shifting algorithm used in interferometry; and
 processing means to calculate by phase-shifting analysis the optical characteristics, angle and phase of the transmitted beam from said reconstructed image so as to determine the beam deviation angle generated by the sample.

2. The apparatus according to claim 1, wherein the Schlieren filter has a set of alternating absorbing and transparent sub-elements.

3. The apparatus according to claim 1, wherein the Schlieren filter corresponds to a grating filter.

4. The apparatus according to claim 3, wherein the Schlieren filter corresponds to a linear grating filter.

5. The apparatus according to claim 4, wherein said linear grating filter is a Ronchi grating.

6. The apparatus according to claim 3, wherein the Schlieren filter corresponds to a sinusoidal grating filter.

7. The apparatus according to claim 1, wherein the Schlieren filter corresponds to a grating filter having circular rings or non regular shape.

8. The apparatus according to claim 1, wherein the phase-shifting means comprise moving means for moving the Schlieren filter relative to the transmitted beam produced by the sample so as to create in operating conditions a phase-shift in the transmitted beam.

9. The apparatus according to claim 1, wherein the Schlieren filter comprises a liquid crystal display on which, in operating conditions, the periodic structure can be generated, said liquid crystal display being coupled to an aperture of a defined diameter, said diameter being dependent on the period of the periodic structure.

10. The apparatus according to claim 9, wherein the phase-shifting means correspond to the liquid crystal display on which in operating conditions, phase-shifted periodic structures are successively generated.

11. The apparatus according to claim 1, wherein the period of the Schlieren filter is at least 0.5 mm.

12. The apparatus according to claim 1, wherein the source and the Schlieren filter are configured to provide a ratio (R) of a source dimension to a Schlieren filter period of between about 0.55 and about 1.12.

13. The apparatus of claim 12, wherein the ratio R is between about 0.60 and about 0.87.

14. The apparatus of claim 13, wherein the ratio R is between about 0.64 and about 0.82.

15. The apparatus of claim 14, wherein the ratio R is between about 0.68 and about 0.79.

16. The apparatus according to claim 1, wherein the source and the Schlieren filter are configured to provide a ratio (R) of a source dimension to a Schlieren filter period of about 0.7.

17. The apparatus according to claim 1, further comprising a diffraction element.

18. The apparatus of claim 17, wherein the diffraction element is a diffraction grating configured to split an incident element into three beams of different angles.

19. The apparatus according to claim 17, wherein said diffraction element is arranged in front of the Schlieren filter.

20. The apparatus according to claim 17, wherein the diffraction element is a periodic element defined by a period between about 10 lp/mm and about 150 lp/mm.

21. The apparatus according to claim 17, wherein a distance between the diffraction element and the Schlieren filter is between about 1 mm and about 100 mm.

22. The apparatus according to claim 1, wherein the detecting means correspond to a camera.

23. A method for detecting and measuring a light beam deviation angle created by a sample, the method comprising:

providing a source of a light beam for illuminating said sample so as to have a transmitted beam;

forming an image of said sample from said transmitted beam;

obtaining "Schlieren fringes" from said image using a Schlieren filter; wherein the Schlieren filter comprises a periodic structure of a defined period;

detecting said Schlieren fringes in operating conditions;

shifting the filter with a shift $\phi$ by a fraction of the period of the periodic structure thereby shifting the Schlieren fringes.

24. The method according to claim 23, further comprising the steps of:

providing a sample to be studied;

obtaining at least three successive phase-shifted images of the sample;

collecting said phase-shifted images;

reconstructing a mean image of the sample from said collected phase-shifted images using phase-shifting analysis using a phase-shifting algorithm used in interferometry; and calculating by phase-shifting analysis optical characteristics, angle and phase of the transmitted beam from said reconstructed image so as to determine the beam deviation angle generated by the sample.

25. An apparatus for measuring by the Schlieren technique light beam deviations generated by a sample, said apparatus comprising:

a light source which provides a transmitted beam;

components which form an image of said sample from said transmitted beam;

a Schlieren filter comprising a periodic structure of a defined period;

a detector which detects Schlieren fringes generated by said Schlieren filter;

components which shift the Schlieren fringes, components which acquire a set of at least three successive phase-shifted images;

component which reconstruct a mean image of the sample from said phase-shifted images using a phase-shifting algorithm used in interferometry; and a processor which calculates by said phase-shifting analysis the optical characteristics, angle and phase of the transmitted beam from said reconstructed image so as to determine the beam deviation angle generated by the sample.

* * * * *

UNITED STATES PATENT AND TRADEMARK OFFICE
CERTIFICATE OF CORRECTION

PATENT NO.         : 7,206,079 B2
APPLICATION NO. : 10/861673
DATED              : April 17, 2007
INVENTOR(S)        : Joannes

It is certified that error appears in the above-identified patent and that said Letters Patent is hereby corrected as shown below:

Column 5, Line 13-14, delete "a.α (x,y)+b°" and insert -- a.α (x,y)+b --.

Column 12, Line 45, after "by" delete "said".

Signed and Sealed this

Thirteenth Day of May, 2008

JON W. DUDAS
*Director of the United States Patent and Trademark Office*